US012403170B2

(12) United States Patent
Shin et al.

(10) Patent No.: US 12,403,170 B2
(45) Date of Patent: Sep. 2, 2025

(54) **PHARMACEUTICAL COMPOSITION CONTAINING *SAURURUS CHINENSIS* FRACTION, AND PREPARATION METHOD THEREOF**

(71) Applicants: PHARMACOBIO, INC., Gyeonggi-do (KR); KYONGGI UNIVERSITY INDUSTRY & ACADEMIA COOPERATION FOUNDATION, Gyeonggi-do (KR)

(72) Inventors: Kwang-Soon Shin, Gyeonggi-do (KR); Yang-Kook Rho, Gyeonggi-do (KR)

(73) Assignees: PHARMACOBIO, INC, Gyeonggi-Do (KR); KYONGGI UNIVERSITY INDUSTRY & ACADEMIA COOPERATION FOUNDATION, Gyeonggi-Do (KR)

( * ) Notice: Subject to any disclaimer, the term of this patent is extended or adjusted under 35 U.S.C. 154(b) by 324 days.

(21) Appl. No.: 18/010,071

(22) PCT Filed: Jun. 17, 2021

(86) PCT No.: PCT/KR2021/007582
§ 371 (c)(1),
(2) Date: Dec. 13, 2022

(87) PCT Pub. No.: WO2021/256865
PCT Pub. Date: Dec. 23, 2021

(65) Prior Publication Data
US 2023/0218701 A1   Jul. 13, 2023

(30) Foreign Application Priority Data
Jun. 17, 2020   (KR) .................. 10-2020-0073480

(51) Int. Cl.
*A61K 36/78* (2006.01)
*A61P 1/00* (2006.01)

(52) U.S. Cl.
CPC .............. *A61K 36/78* (2013.01); *A61P 1/00* (2018.01); *A61K 2236/19* (2013.01); *A61K 2236/333* (2013.01); *A61K 2236/51* (2013.01)

(58) Field of Classification Search
None
See application file for complete search history.

(56) References Cited

U.S. PATENT DOCUMENTS

2003/0045564 A1* 3/2003 Kim .................. C07D 209/80
514/410
2018/0085415 A1   3/2018 Cardelli

FOREIGN PATENT DOCUMENTS

| CN | 110467687 A | 11/2019 |
|---|---|---|
| JP | 2004-520294 A | 7/2004 |
| JP | 2021-031424 A | 3/2021 |
| KR | 10-2004-0008975 A | 1/2004 |
| KR | 20050076225 A | 7/2005 |
| KR | 10-2010-0090737 A | 8/2010 |
| KR | 10-2014-0109644 A | 9/2014 |
| KR | 10-1482661 B1 | 1/2015 |
| KR | 20150034364 A | 4/2015 |
| KR | 10-2015-0142213 A | 12/2015 |
| KR | 20170067055 A | 6/2017 |
| WO | WO-2011/099665 A1 | 8/2011 |
| WO | WO-2013/191342 A1 | 12/2013 |

OTHER PUBLICATIONS

Choi (KR 20140143583 A—English translation)—Dec. 2014.*
Jeong (KR 20100090737 A—English translation)—Aug. 2010.*
Kim (KR 20180012955 A—English translation)—Feb. 2018.*
Johansson, M. E. V. (2014). Mucus Layers in Inflammatory Bowel Disease. Inflammatory Bowel Diseases, 20(11), 2124-2131.
International Search Report from corresponding PCT Application No. PCT/KR2021/007582, dated Oct. 18, 2021.
Notification of the First Office Action From Corresponding Chinese Application No. 202180043349.1, Dated Jun. 13, 2023.
Sui, J. et al. (2020). Research Progress on Chemical Composition and Pharmacological Effects of Saururus chinensis and Predictive Analysis on Quality Marker. Science and Technology of Food Industry, 41(18), 353-367.
Kang Chang-S00 et al: "Study on the Antioxidative and Physiological Activities of Saururus chinensis Extract", Journal of Life Science, Korean Society of Life Science, KR, vol. 22, No. 6, Jun. 30, 2012 (Jun. 30, 2012), pp. 807-814, XP053031117.
Yeun-Kyung Lee et al: "Inhibition of DNA topoisomerases I and II and cytotoxicity by lignans from Saururus chinensis", Archives of Pharmacal Research, vol. 32, No. 10, Oct. 1, 2009 (Oct. 1, 2009 ), pp. 1409-1415, XP055600148.
Meng Xue et al: "Anti-inflammatory effects of Saururus chinensis aerial parts in murine macrophages via induction of heme oxygenase-1", Experimental Biology and Medicine, vol. 241, No. 4, Feb. 8, 2016, pp. 396-408, XP93112894.
Extended European Search Report from corresponding EP Patent Application No. 21826722.7, dated Jan. 25, 2024.
Office Action from corresponding JP Patent Application No. 2022-578876, dated Jan. 9, 2024.

* cited by examiner

*Primary Examiner* — Susan Hoffman
(74) *Attorney, Agent, or Firm* — Harness, Dickey & Pierce, P.L.C.

(57) ABSTRACT

The present disclosure relates to a pharmaceutical composition for preventing, treating or ameliorating inflammatory bowel disease, containing, as an active ingredient, a specific solvent fraction obtained from *Saururus chinensis*; and a preparation method therefor.

5 Claims, 8 Drawing Sheets

PHARMACEUTICAL COMPOSITION CONTAINING *SAURURUS CHINENSIS* FRACTION, AND PREPARATION METHOD THEREOF

CROSS-REFERENCE TO RELATED APPLICATIONS

This application is a national phase application of PCT Application No. PCT/KR2021/007582 filed on Jun. 17, 2021, which claims priority to Korean Patent Application No. 10-2020-0073480 filed on Jun. 17, 2020. The entire disclosures of the applications identified in this paragraph are incorporated herein by references.

TECHNICAL FIELD

The present disclosure relates to a preparation method of an active fraction of *Saururus chinensis*. The present disclosure also relates to a pharmaceutical composition comprising a solvent fraction of *Saururus chinensis* prepared by a specific preparation method. The present disclosure further relates to a medical use of a solvent fraction of *Saururus chinensis* for treating inflammatory bowel disease.

BACKGROUND ART

Dysregulation of inflammatory response can lead to the development of chronic inflammation, which causes various diseases such as rheumatoid arthritis, atherosclerosis and asthma. Colitis is a disease in which inflammation occurs in the large intestine, and includes inflammatory bowel disease (IBD), irritable bowel syndrome (IBS), and the like. Inflammatory bowel disease (IBD) is represented by ulcerative colitis (UC) and Crohn's disease (CD). Globally, the prevalence of inflammatory bowel disease has tendency to increase, with a rate of increase being higher in Asian countries than in Western countries. Inflammatory bowel disease is a chronic disease that requires lifelong management.

Mucosal biopsies of patients with IBD show increased expression of pro-inflammatory cytokines, chemokines, and ICAM-1 (Intercellular Adhesion Molecule 1) and loss of mucous, and a reduction in tight junctions between epithelial cells. A representative drug currently used for the treatment of inflammatory bowel disease include 5-aminosalicylic acid, corticosteroid, immunomodulator, anti-tumor necrosis factor-α agent (anti TNF-α), and the like. Because they exert their effects through mutually different mechanisms of action, they are used in stages according to clinical guidelines, but they do not appear to be a fundamental therapeutic drug, and various side effects have been reported.

Mucosal healing has recently emerged as a therapeutic goal of inflammatory bowel disease. The greatest features of patients with inflammatory bowel disease is that mucosal production of the colon is lowered. The absence of a mucous layer allows bacteria to reach the intestinal epithelial cells directly, which causes a severe inflammatory response. (Johansson, M. E. (2014) Mucus layers in inflammatory bowel disease. Inflammatory bowel diseases 20, 2124-2131). In order to fundamentally improve intestinal function, mucosal production must be restored, and the robustness of tight junction between intestinal epithelial cells is also of great importance. In this regard, recently, research on mucosal production has been actively conducted. Therefore, in order to treat IBD and maintain healthy intestinal function, inhibition of inflammation, normal restoration of the mucous layer, and restoration of tight junction robustness of intestinal epithelial cells should be performed properly. However, there is currently no effective therapeutic agent for inflammatory bowel disease, and only symptom-relieving agents are prescribed. As the number of patients is increasing, there is an urgent need to develop a therapeutic agent that meets these needs.

Meanwhile, *Saururus chinensis* (also called Sambaekcho) is a perennial herbaceous plant belonging to the family Saururaceae, which is known in folklore to have various effects in the whole plant or the roots and leaves.

DETAILED DESCRIPTION OF THE INVENTION

Technical Problem

Therefore, it is an object of the present disclosure to provide a pharmaceutical or health functional food composition for treating, ameliorating or preventing inflammatory bowel disease using *Saururus chinensis*.

It is another object of the present disclosure to provide a method for preparing an extract or solvent fraction of *Saururus chinensis* having excellent therapeutic, ameliorating or preventive effects on inflammatory bowel disease.

It is another object of the present disclosure to provide a medical use of a solvent fraction of *Saururus chinensis* prepared by a specific preparation method.

It is yet another object of the present disclosure to provide a method of treating inflammatory bowel disease, comprising administering a pharmaceutical composition for treating, ameliorating or preventing inflammatory bowel disease using *Saururus chinensis* to an individual in need thereof.

Technical Solution

According to one embodiment of the present disclosure, there is provided a method (method 1) for preparing a solvent fraction of *Saururus chinensis* (SCEP2) effective for inflammatory bowel disease, the method comprising the steps of:

(S1) extracting *Saururus chinensis* with a 50-90 volume % ethanol aqueous solution,
(S2) adding purified water to the residue remaining after the extraction, and heating to 70-100° C., preferably 80-100° C., more preferably 90-100° C.,
(S3) enzymatically treating the result of the step S2,
(S4) removing the residue in the extract and filtering,
(S5) adding ethanol to the filtrate of the step S4 to form a precipitate, and
(S6) obtaining the precipitate.

In the method 1 according to the present disclosure, the enzyme serves to separate the active polysaccharide component present in *Saururus chinensis*, and preferably, one or more enzymes selected from the group consisting of pectinase (or polygalacturonase), pectinesterase, pectin lyase, arabinanase, xylanase, beta-glucanase, cellulase can be used alone or in combination. More preferably, the enzyme may be polygalacturonase, pectin lyase or a mixture thereof, and even more preferably, the enzyme is a mixture of polygalacturonase and pectin lyase.

For example, one or more enzymes selected from the group consisting of Pectinex® Ultra SP-L(polygalacturonase), Pectinex® Ultra MASH(pectin lyase), Rapidase C80Max (pectinase, arabinanase), Viscozyme L (endo-1,3 (4)-beta-glucanase), Xylanase, cellulase, hemicellulase, arabinanase), Pectinex 5XL (pectin lyase, polygalacturonase, pectinesterase) and the like, which are commercially available enzymes, can be used alone or in combination. More preferably, Pectinex® Ultra SP-L and Pectinex® Ultra MASH are used alone or in combination.

The enzyme treatment may be performed by adding 0.05-5 parts by weight of the enzyme based on parts by weight of *Saururus chinensis*. When the amount of enzyme is less than 0.05 parts by weight, the amount of enzyme is too small, and the recovery rate of active polysaccharides present in *Saururus chinensis* is reduced, and when the amount of enzyme exceeds 5 parts by weight, the efficacy of the active polysaccharide may be lowered due to excessive enzyme action, which is thus not preferable.

The reaction time during the enzymatic treatment is preferably 6-96 hours, more preferably 12-72 hours. The temperature and pH under the enzymatic treatment are applied under optimal conditions for each enzyme, thereby capable of obtaining the active polysaccharide component with the highest recovery rate, which is thus preferable. When the enzyme treatment reaction time is less than 6 hours, the time required for the enzyme treatment is too short, reducing the recovery rate, and when the reaction time is more than 96 hours, the efficacy of the active polysaccharide may be lowered due to excessive enzyme treatment, which is thus not preferable.

In the method 1 according to the present disclosure, preferably, the step S5 is a step of concentrating the filtrate, adding more (preferably, 2-8 times by volume) ethanol than the concentrate and stirring the mixture to form a precipitate. In this step, the precipitate may be formed by allowing the reaction solution to stand still.

In the method 1 according to the present disclosure, the step of obtaining the precipitate of the step S6 can be performed, for example, by centrifugation. The recovered precipitate can be used as a raw material for producing pharmaceuticals after concentration and freeze-drying.

According to another embodiment of the present disclosure, there is provided a method (method 2) for preparing a solvent fraction of *Saururus chinensis* (SCESII-1) effective for inflammatory bowel disease, the method comprising the steps of:

(S1) extracting *Saururus chinensis* with a 50-90 volume % ethanol aqueous solution,
(S2) filtering and concentrating the extract,
(S3) passing the concentrate through a resin-filled column to separate the components depending on whether or not they are adsorbed to a resin, and
(S4) obtaining components eluted according to the water and ethanol concentration gradient among the components adsorbed on the resin.

More specifically, the three solvent fractions can be obtained as follows.

Fraction 1 (SCESII-1): Elution is started with 20-40 volume % (preferably 30%) ethanol, and stops recovery when the recovered eluate reaches a bed volume of approximately 1.5-2.5 (preferably 2 times) ethanol, and the elution solvent is changed to 60-80 volume % (preferably 70%) ethanol. It is a fraction until the elution solvent is changed to 60-80 volume % ethanol. Preferably, the eluate is allowed to flow at room temperature at a flow rate at which a bed volume (BV) of one time per unit time flows, and the eluate is recovered.

Fraction 2 (SCESII-2): Elution is started with 60-80 volume % (preferably 70%) ethanol and recover it. When the eluate reaches a bed volume (BV) of about 1.5-2.5 (preferably 2 times), the recovery is stopped, and the elution solvent is changed to 100% ethanol.

Fraction 3 (SCESII-3): Elution is started with 100% ethanol and recover it. Recover the eluate until it reaches a bed volume (BV) of about 2.5-3.5 (preferably 3 times).

According to yet another embodiment of the present disclosure, there is provided a method (method 3) for preparing a solvent fraction of *Saururus chinensis* (SCESII-4) effective for inflammatory bowel disease, the method comprising the steps of:

(S1) extracting *Saururus chinensis* with a 50-90 volume % ethanol aqueous solution,
(S2) filtering and concentrating the extract,
(S3) separating the concentrate with a resin according to polarity, and
(S4) obtaining components not adsorbed to a column during separation of the resin.

It has been known that *Saururus chinensis* extract has various effects such as anti-oxidation, anti-cancer, and anti-inflammatory effects, but according to the results confirmed by the present inventors, the conventional *Saururus chinensis* extract had almost no effect on inflammatory bowel disease. However, unusually, the solvent fraction of *Saururus chinensis* obtained by a specific preparation method exhibited a surprising effect in treating or ameliorating inflammatory bowel disease, unlike the conventional *Saururus chinensis* extract. The present inventors confirmed that the active solvent fraction *Saururus chinensis* prepared by a specific preparation method exhibits effects such as therapeutic effects on DSS-induced colitis in mice, anti-inflammation effects, increased mucin production capacity, and enhanced tight junction robustness of intestinal epithelial cells, and confirmed its usefulness in the treatment of inflammatory bowel disease through examination of colon tissue induced by inflammatory bowel disease with DSS. The present inventors further confirmed that the solvent fraction of *Saururus chinensis* by a specific preparation method according to the present disclosure inhibits the activity of inflammatory cytokines TNF-α, IL-1β, IL-6, etc., thereby completing the present disclosure.

As for the *Saururus chinensis, Saururus chinensis* (Sambaekcho) belonging to the family Sauruaceae can be used.

Preferably, in the methods 1 to 3 according to the present disclosure, the aqueous ethanol solution is 60-80 volume % ethanol aqueous solution. More preferably, in the methods 1 to 3 according to the present disclosure, the aqueous ethanol solution is 65-75 volume % ethanol aqueous solution.

In the methods 2 and 3 according to the present disclosure, preferably, the residue recovered in the step S1 can be extracted similarly under the extraction conditions of step S1 to recover the extract, and this extract can be used in combination with the extract in step S1.

In the methods 2 and 3 according to the present disclosure, preferably, High porous type synthetic adsorbent of Styrene and DVB (Divinyl benzene) copolymer (e.g., Amberlite XAD-2, Amberlite XAD-4, Amberlite XAD-16N, Amberlite XAD-1180N, TRILITE® GSH-20, TRILITE GSP-25 TRILITE GSP-50, TRILITE GSP-07, DIAION HP20), porous synthetic adsorbent of nonionic aliphatic acrylic polymer (e.g., Amberlite XAD-7HP) and the like can be used as the resin. Preferably, in the methods 2 and 3 according to the present disclosure, DIAION's HP20 is used as the resin.

In order to remove remaining small amount of alcohols and organic solvents so as to make them suitable for use as pharmaceutical raw materials, the solvent fraction of *Saururus chinensis* according to the present disclosure can be prepared in a powder state using a conventional drying method such as vacuum drying, spray drying, or freeze drying. Specifically, the solvent fraction of *Saururus chinensis* may be in the form of a concentrated liquid or lyophilized powder. According to one embodiment of the present disclosure, the solvent fraction of *Saururus chinensis* according to the present disclosure may be a soft extract in concentrated liquid form.

The present disclosure also provides a pharmaceutical or health functional food composition comprising a solvent fraction of *Saururus chinensis*, which is obtained by any one of the methods 1 to 3 according to the present disclosure.

The present disclosure further provides a pharmaceutical or health functional food composition for preventing, treating or ameliorating inflammatory bowel disease, comprising a solvent fraction of *Saururus chinensis*, which is obtained by any one of the methods 1 to 3 according to the present disclosure.

As used herein, the term "inflammatory bowel disease" is a generic term for diseases that cause inflammation in the intestine tract, and specifically, it may be a chronic recurrent inflammatory disease caused by dysregulation of the immune system in the small intestine and/or large intestine. The inflammatory bowel disease includes ulcerative colitis, Crohn's disease, irritable bowel syndrome (IBS), and the like.

The pharmaceutical or health functional food composition of the present disclosure can be formulated into in a dosage form for oral administration, for example, tablets, troches, lozenges, water-soluble or oily suspensions, powders or granules, emulsions, hard or soft capsules, syrups or elixirs, or the like according to a conventional method for preventing or treating inflammatory bowel disease.

To formulate into the dosage form such as tablets, capsules and the like, the following may be contained: excipients such as lactose, saccharose, sorbitol, mannitol, starch, lactose, microcrystalline cellulose, etc., binders such as polyvinylpyrrolidone, hydroxypropylmethylcellulose, etc., disintegrants such as dicalcium phosphate, crospovidone, etc., lubricants such as magnesium stearate, calcium stearate, sodium stearyl fumarate, polyethylene glycol wax, etc. In the case of the capsule dosage form, liquid carriers such as fatty oil may be contained in addition to the above-mentioned materials.

Also, the pharmaceutical composition of the present disclosure may be parenterally administered. The parenteral administration may be performed by means of subcutaneous injection, intravenous injection, intramuscular injection or intrathoracic injection method. To formulate into the dosage form for parenteral administration, said composition may be prepared into solution by being mixed in water with stabilizers or buffer agents, and then may be formulated again into a unit form for administration of ampoule or vial.

A dosage of the pharmaceutical or health functional food composition according to the present disclosure need to be an amount effective to exhibit sufficient therapeutic or prophylactic effects. The term "effective amount" refers to an amount which is sufficient to treat the disease at a reasonable benefit/risk ratio applicable to medical treatment, and a level of effective dose may be variously selected by those skilled in the art according to factors such as a formulation method, a patient's condition, weight, gender and age, a severity of disease, a drug form, an administration route and period, an excretion rate, reaction sensitivity, etc. The effective amount may vary depending on a route of treatment, a use of excipients and a possibility of being used with other drugs, as recognized by those skilled in the art.

A dosage or dose of the solvent fraction of *Saururus chinensis* according to the present disclosure may be diversified according to a patient's age, physical condition, body weight, etc., but may be preferably administered within a range of 10 to 100 mg/kg (body weight)/day in general. And such administration may be performed once a day or divided into several times a day within the range of daily effective inputs.

The health functional food composition according to the present disclosure can be ingested by being included in various foods. For example, it can be ingested by being included in meats, sausages, breads, chocolates, candies, snacks, confectioneries, pizzas, instant noodles, other noodles, chewing gums, dairy products including ice creams, various types of soup, beverages, teas, health drinks, alcohol beverages, vitamin complexes and the like.

According to still yet embodiment of the present disclosure, there is provided a method for treating, preventing or ameliorating inflammatory bowel disease, the method comprising administering a pharmaceutically or prophylactically effective amount of the solvent fraction of *Saururus chinensis*, which is prepared by a specific preparation method of the present disclosure, to an individual in need of treatment, prevention or amelioration of inflammatory bowel disease. Preferably, the individual is human.

Advantageous Effects

The present disclosure provides a method for preparing a solvent fraction of *Saururus chinensis* useful for the treatment, amelioration or prevention of inflammatory bowel disease. The present disclosure also provides a pharmaceutical or health functional food composition for treating, ameliorating or preventing inflammatory bowel disease comprising, as an active ingredient, a solvent fraction of *Saururus chinensis* prepared according to the preparation method of the present disclosure.

BRIEF DESCRIPTION OF THE DRAWINGS

The following drawings attached to the present specification illustrate preferred embodiments of the present disclosure, and serve to further understand the technical concept of the present disclosure together with the above-described contents of the present disclosure, and the present disclosure should not be construed as being limited only to the matters set forth in such drawings.

DETAILED DESCRIPTION OF THE EMBODIMENTS

Hereinafter, the present disclosure will be described in detail with reference to Examples and the like for better understanding. However, the examples of the present disclosure can be modified in various ways, and they should not be interpreted as limiting the scope of the invention. The examples of the present disclosure are just for better understanding of the invention to persons having ordinary skill in the art.

Preparation of Solvent Fractions of *Saururus chinensis*

Figure 1:
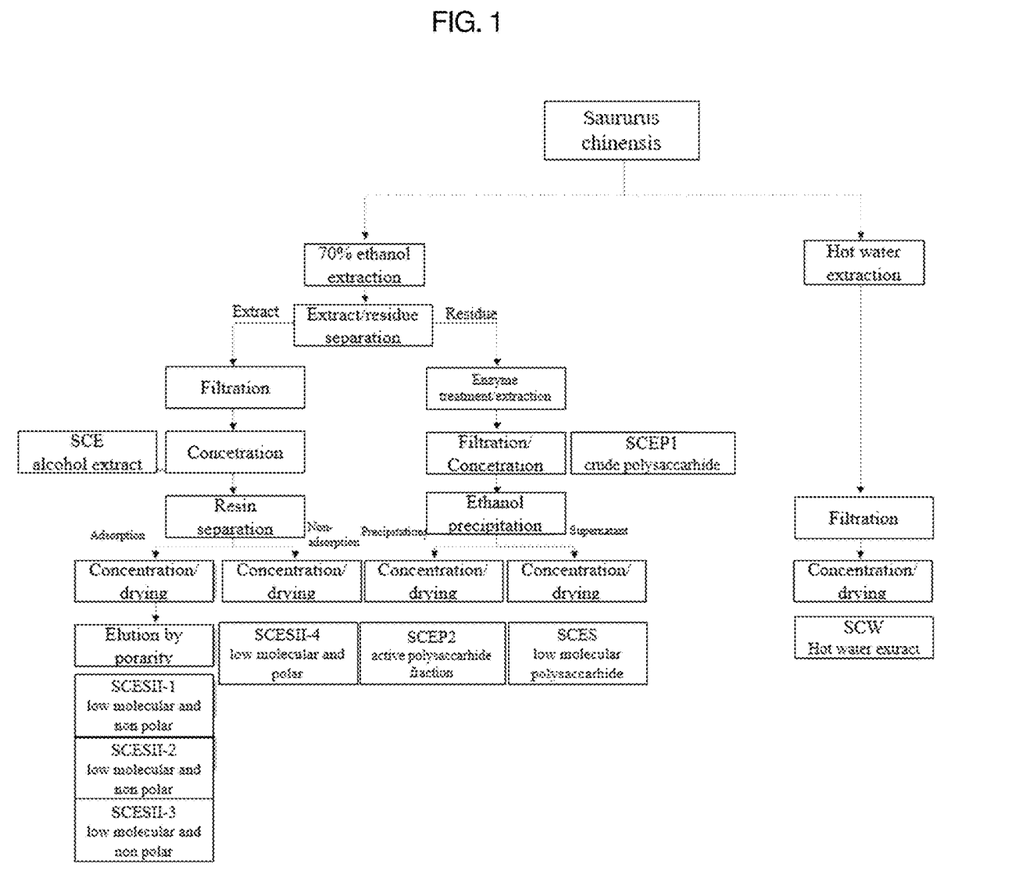
FIG. 1 schematically shows the process of preparing a solvent fraction of *Saururus chinensis*.

Various fractions were prepared as shown in FIG. 1.

Example 1: Preparation of *Saururus chinensis* Hot Water Extract (SCW)

The dried and pulverized *Saururus chinensis* was mixed with 20-fold volume of purified water, and extracted at 100° C. for 2 hours. After extraction, the residue was removed using an extraction cloth, and the extract was filtered with Whatman No. 2 filter paper. The filtrate was concentrated using a vacuum concentrator, and then freeze-dried to prepare a *Saururus chinensis* hot water extract (SCW).

Example 2: Preparation of Various *Saururus chinensis* Organic Solvent Extracts (SCE, SCESII-1, SCESII-2, SCESII-3, SCESII-4)

The dried and pulverized *Saururus chinensis* was mixed with 10-fold volume of 70% (v/v) ethanol aqueous solution, and extracted at 70° C. for 2 hours. After filtration with an extraction cloth, the filtered residue was extracted once more under the same conditions. The extract was filtered with Whatman No. 2 filter paper and concentrated using a vacuum concentrator. This was called 70% ethanol extract concentrate SCE. The SCE extract was passed through a column filled with synthetic resin HP20. All components that were not adsorbed to the resin were recovered using purified water. This component was called SCESII-4. In the next step, the components adsorbed to the resin were eluted in the order of purified water ~30 volume % ethanol, 30-70 volume % ethanol, and 70-100 volume % ethanol, and was recovered according to the polarity of the elution solvent. These were called SCESII-1, SCESII-2, and SCESII-3 according to the order in which they were first eluted.

Example 3: Preparation of *Saururus chinensis* Crude Polysaccharide SCEP1, Active Polysaccharide SCEP2 and Low Molecular Saccharide SCES Fractions

*Saururus chinensis* was extracted with 70% ethanol aqueous solution, and the remaining residue was again mixed with 20-fold volumes of purified water and stirred at 100° C. for 2 hours. Enzyme (1:1 weight ratio of Pectinex® Ultra SP-L and Pectinex® Ultra MASH) was added and reacted with stirring at 55° C. for 72 hours. The enzyme reaction solution was inactivated at 100° C. for 30 minutes. After removing the residue using an extraction cloth, the extract was filtered with Whatman No. 2 filter paper. This filtrate was called crude polysaccharide SCEP1. After the filtrate was concentrated, ethanol of 4 times the volume of the concentrate was added, stirred for 30 minutes, and then left at room temperature for 24 hours to form a precipitate. The precipitate was centrifuged to recover the precipitate and the supernatant, respectively. The recovered precipitate was concentrated and then freeze-dried to prepare a SCEP2 active polysaccharide fraction of *Saururus chinensis*, and the supernatant was concentrated and then freeze-dried to prepare a low molecular-weight sugar fraction of *Saururus chinensis* SCES.

Experimental Example 1: Evaluation of Anti-Inflammatory Effect in Intestinal Inflammation Model A study was conducted on the inhibition and therapeutic effect of the *Saururus chinensis* active ingredient fraction. Inflammatory bowel disease was induced with dextran sodium sulfate (DSS) in the BALB/c mouse model. One hundred 8-week-old male BALB/c mice were purchased for the experiment and randomly divided into 9 groups. To induce acute colitis in mice, DSS was dissolved at 5% in drinking water, and BALB/c mice were watered ad libitum for 7 days. Normal control group (NT: not treated) was provided with drinking water ad libitum. After 1 day of DSS watering, the normal control group and the negative control group (NC) ingested singly with 5% DSS were dissolved in distilled water, and the sample group was dissolved in distilled water at the doses listed in Table 1 below, and administered orally once a day for 9 days.

TABLE 1

| Group | Dietary method |
|---|---|
| Normal group Not treated(NT) group | Group in which neither dextran sulfate sodium (DSS) nor sample was administered |
| Negative control (NC) group | Dextran sulfate sodium (DSS)-treated inflammatory bowel disease induction group |
| Experiment group *Saururus chinensis* alcohol extract SCE | SCE 2.0 mg/mouse + dextran sulfate sodium (DSS) were treated |
| Experiment group *Saururus chinensis* water extract SCW | SCW 2.0 mg/mouse + dextran sulfate sodium (DSS) were treated |
| Experiment group Low molecular and non-polar SCESII-1 | SCESII-1 2.0 mg/mouse + dextran sulfate sodium (DSS) were treated |
| Experiment group Low molecular and non-polar SCESII-2 | SCESII-2 2.0 mg/mouse + dextran sulfate sodium (DSS) were treated |
| Experiment group Low molecular and non-polar SCESII-3 | SCESII-3 2.0 mg/mouse + dextran sulfate sodium (DSS) were treated |
| Experiment group Low molecular and non-polar SCESII-4 | SCESII-4 2.0 mg/mouse + dextran sulfate sodium (DSS) were treated |
| Experiment group Low molecular saccharide SCES | SCES 2.0 mg/mouse + dextran sulfate sodium (DSS) were treated |
| Experiment group Crude polysaccharide SCEP1 | SCEP-1 2.0 mg/mouse + dextran sulfate sodium (DSS) were treated |
| Experiment group Active polysaccharide SCEP2 | SCEP-2 2.0 mg/mouse + dextran sulfate sodium (DSS) were treated |

The disease activity index (DAI) was calculated based on the score shown in Table 2 below after visual confirmation of the weight loss, loose or soft stool, bloody stool, and the presence or absence of blood in the anus at intervals of 2 days.

$$DAI = (\text{weight loss score}) + (\text{stool consistency score}) + (\text{blood in stool score}) + (\text{blood in anus score}) \quad \text{Equation:}$$

Disease Activity Index (DAI) Scoring System

TABLE 2

| Score | Weight | Stool consistency | Blood in stool | Blood in anus |
|---|---|---|---|---|
| 0 | — | Normal | Normal | Normal |
| 1 | 1-5% | — | trace | trace |
| 2 | 5-10% | Loose stool | Hemoccult + | Hemoccult + |
| 3 | 10-20% | — | Hemoccult ++ | Hemoccult ++ |
| 4 | >20% | Diarrhea | Gross bleeding | Gross bleeding |

The evaluation results are shown in Table 3 below.

TABLE 3

| Average | 2-day | 4-day | 6-day | 8-day |
|---|---|---|---|---|
| NT Not treated | 0.2 ± 0.4472 | 0.8 ± 1.0954 | 1 ± 1 | 0.6 ± 0.8944 |
| NC DSS treated | 2 ± 0.7071 | 1.6 ± 2.0736 | 10.2 ± 1.7889 | 14.8 ± 1.3038 |
| SCE alcohol extract | 1.4 ± 1.1402 | 1 ± 0.7071 | 9.4 ± 2.3022 | 13.2 ± 1.7889 |
| SCE water extract | 1.8 ± 0.5477 | 2.4 ± 0.8944 | 9.2 ± 0.8944 | 12.8 ± 2.1679 |
| SCESII-1 low molecular and non-polar | 0 ± 0 | 2.4 ± 0.8944 | 6.6 ± 0.5477 | 8.4 ± 1.1402 |
| SCESII-2 low molecular and non-polar | 0.4 ± 0.5477 | 2.6 ± 0.8944 | 6.6 ± 0.8944 | 9.2 ± 2.1679 |
| SCES II-3 low molecular and non-polar | 1 ± 1 | 2.2 ± 1.6432 | 8.2 ± 3.2711 | 12.4 ± 1.5166 |
| SCESII-4 low molecular polar | 0 ± 0 | 2 ± 0 | 6 ± 0 | 9.2 ± 2.1679 |
| SCES low molecular saccharide | 1 ± 1 | 1.6 ± 0 | 6.6 ± 1.8166 | 9.6 ± 2.0736 |
| SCEP1 crude polysaccharide | 1 ± 1 | 1.2 ± 1.6432 | 6.2 ± 3.2711 | 10.4 ± 1.5166 |
| SCEP2 active polysaccharide | 2 ± 0 | 1.2 ± 1.0954 | 5.8 ± 1.7889 | 7.6 ± 0.5477 |

As a result of measuring the DAI change of each administration group, the DAI score increased from day 2 of all groups except for the normal control group, but the low molecular active substance fraction SCESII-1 and the active polysaccharide fraction SCEP2 had a significantly lower DAI score than the negative control group (NC) on the 8th day, indicating an inhibitory effect on colitis. On the other hand, the other solvent fractions and *Saururus chinensis* water extract had almost no effect.

DAI is measured using factors such as body weight, stool condition, and bloodstain level, and thus, the DAI could be a more important evaluation factor.

Figure 2A:
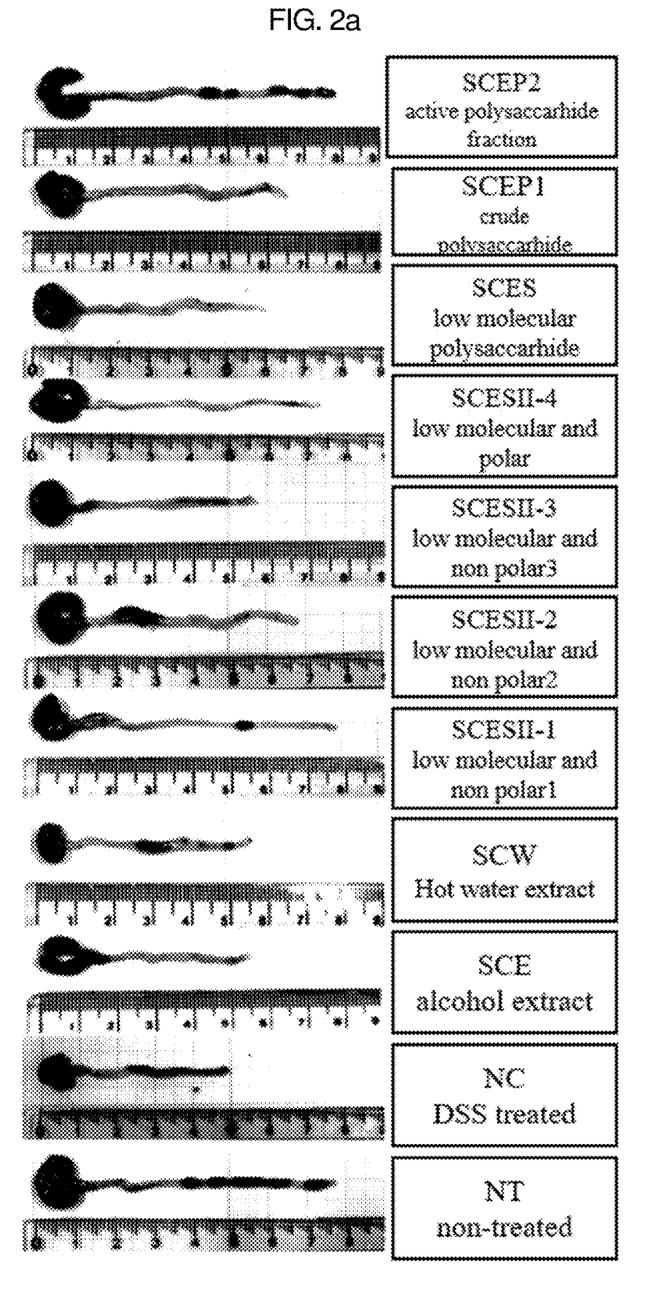
FIG. 2a and FIG. 2b are the results of evaluating the mouse colon length on the 10th day of the intestinal inflammation model evaluation after administration of the *Saururus chinensis* fraction (n=8).
Figure 2B:
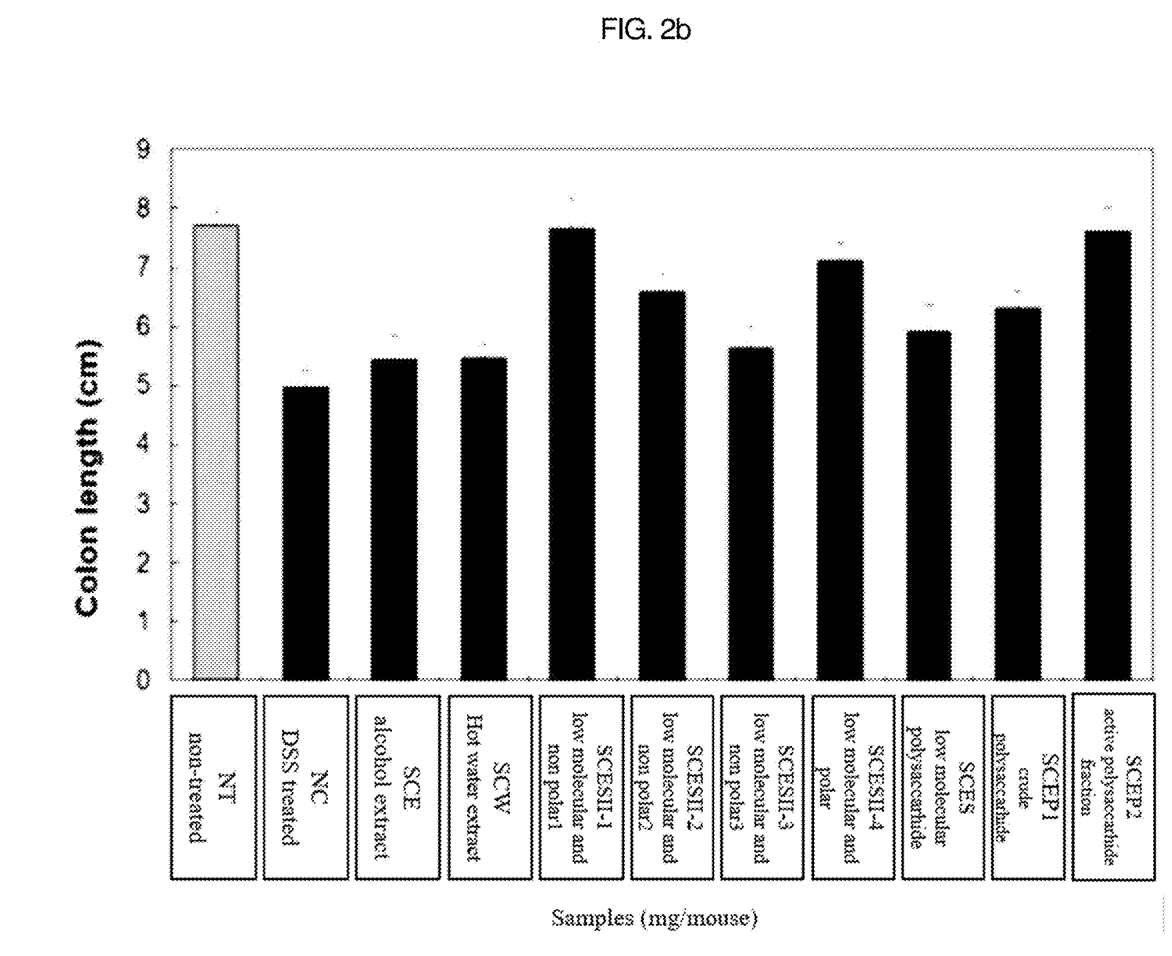

Mice were sacrificed on the 10th day of the experiment, and the length of the large intestine and small intestine and the weight of the spleen were measured and evaluated. The results are collectively shown in FIG. 2.

Mice were sacrificed and the length of the large intestine was measured. As a result, the NC ingested with 5% DSS alone has approximately 32% reduction in colon length as compared to the negative control group that did not ingest DSS, but the low molecular active fraction SCESII-1, SCESII-4, and the active polysaccharide fraction SCEP2 recovered to a length almost similar to that of the normal group NT. This shows that colitis has improved remarkably as compared to the negative control group. In particular, the active polysaccharide fraction SCEP2 and the low molecular active fraction SCESII-1 derived from *Saururus chinensis* had very similar colon lengths between mice, so it was considered that the reliability of the experiment was high. On the other hand, it was confirmed that the other extracts or fractions experimental groups, including *Saururus chinensis* water extract, alcohol extract, etc. showed the length of the large intestine similar to that of NC or showed a minute recovery, thereby having no effects.

In particular, in the 5% DSS single intake group (NC), all mice had diluted stool and bloody stool was observed, whereas the active polysaccharide fraction SCEP2 had less watery stool than NC, and only occult blood was observed in 3 mice. This is a result showing that the active polysaccharide derived from *Saururus chinensis* has an excellent therapeutic effect on colitis. Taken together, the above results show that the active polysaccharide fraction SCEP2 and the low molecular active fraction SCESII-1 had a DAI score of 5% DSS alone recovered to a normal level, unlike the negative control group (NC), and the length of the large intestine is relatively long, thereby having colitis inhibitory activity.

Experimental Example 2: Observation of Histological Changes in Large Intestine after Administration of the Solvent Fraction of *Saururus chinensis*

After autopsy, the excised colon was fixed in a 10% formaldehyde solution for histological examination, and then paraffin-embedded through a general tissue treatment process. Each embedded tissue was sectioned 5.0 µm with a microtome (Leica, Wetzlar, Germany), followed by Alcian Blue staining. Each slice was treated with canadian balsam and observed with an Olympus BX53 microscope (Olympus Corp., Tokyo, Japan). The results are shown in FIG. 3.

Figure 3:
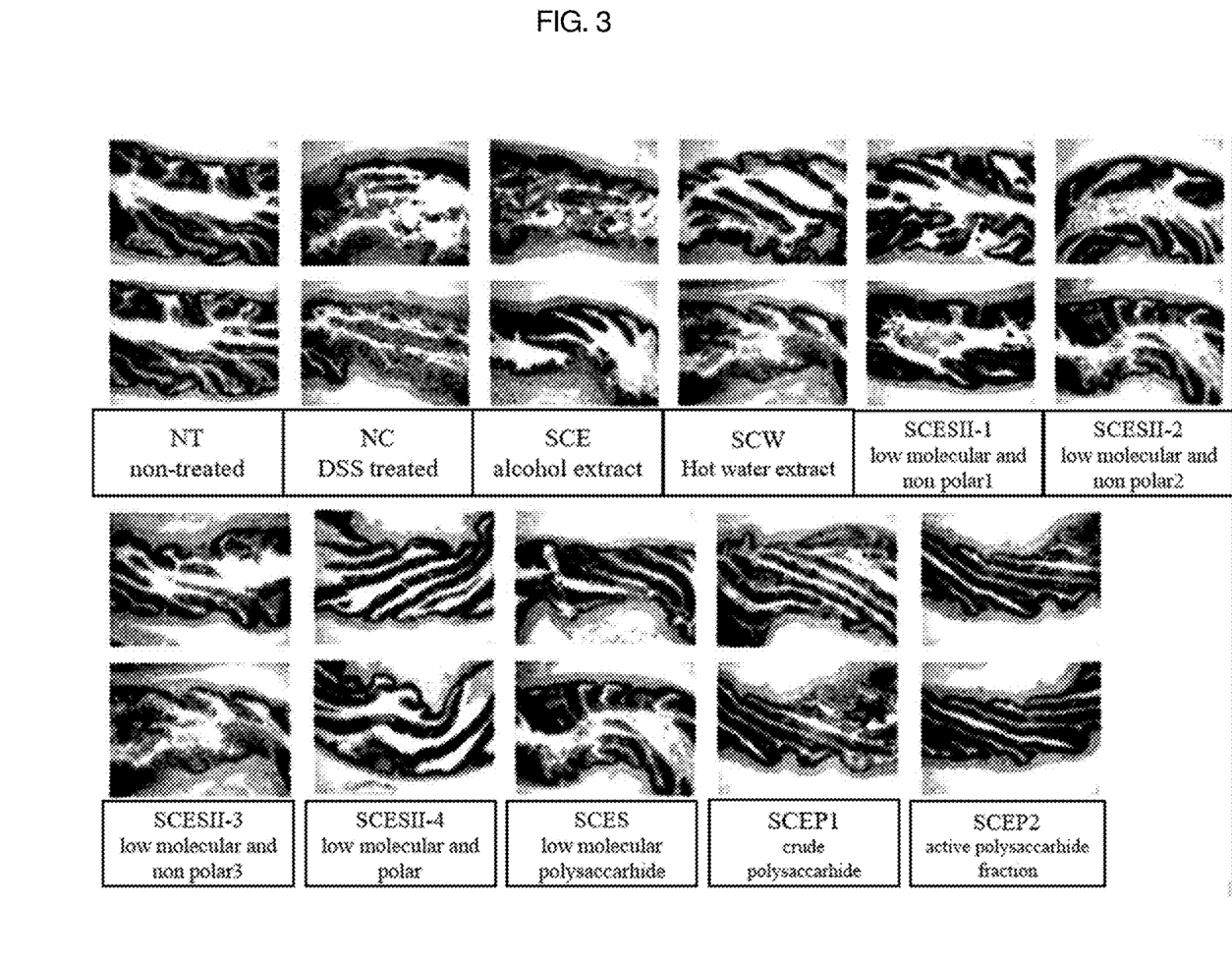
FIG. 3 is the results of observing the histological change of the colon after administration of the solvent fraction of *Saururus chinensis*.

As shown in FIG. 3, in the group treated with dextran sodium sulfate, tissue damage due to inflammation was severe, inflammation continued to the mucous membrane, and the entire intestinal gland and epithelial cells were severely damaged.

However, in the group administered with the active polysaccharide fraction SCEP2, the low molecular active fraction SCESII-1, and the low molecular active fraction SCESII-4, markedly recovered tissue findings were found.

Experimental Example 3: Evaluation of MPO and TNF-α Contents in the Colon Tissue after Administration of Solvent Fraction of *Saururus chinensis*

Figure 4:
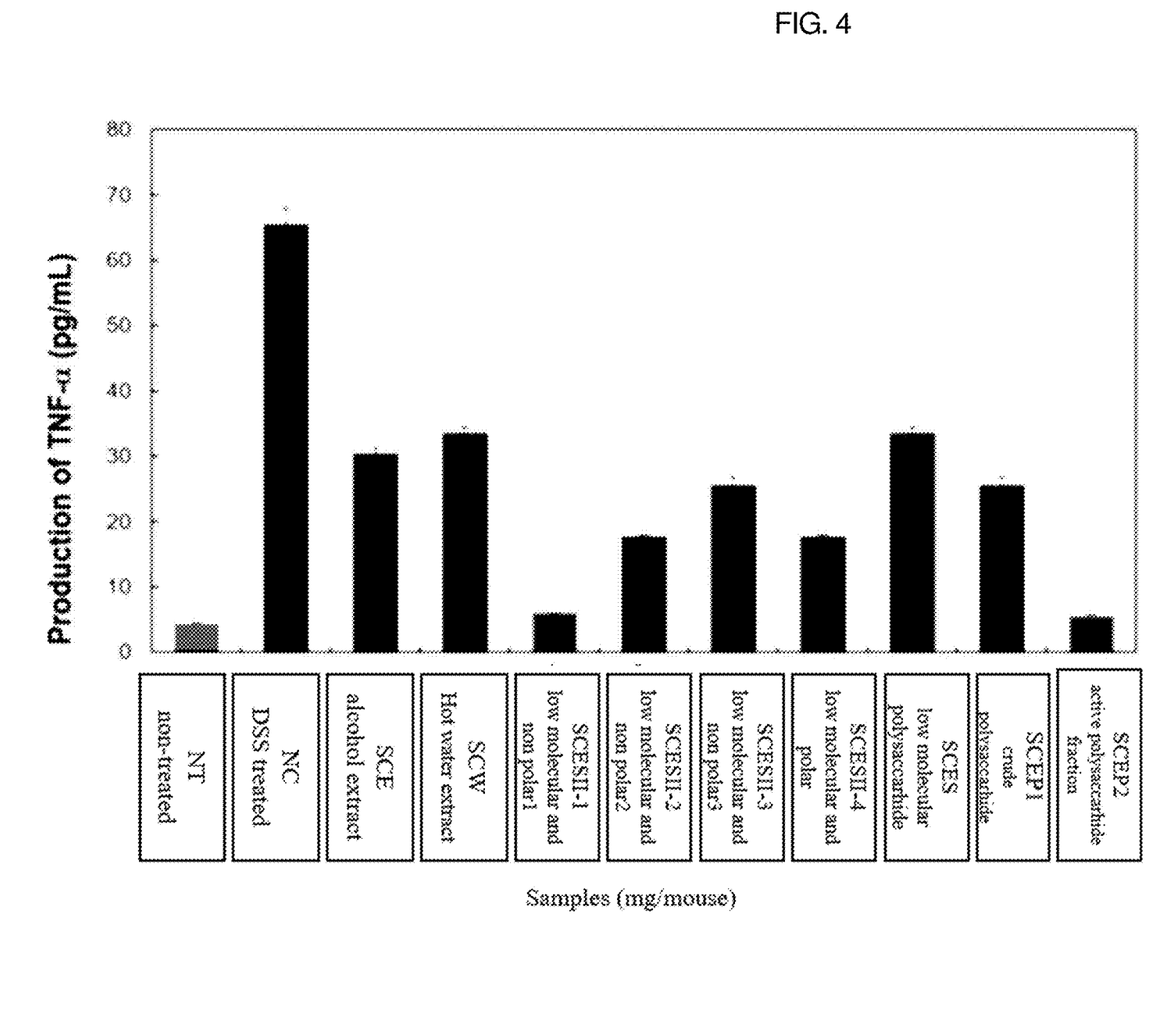
FIG. 4 is the evaluation results of TNF-α content in colon tissue after administration of the solvent fraction of *Saururus chinensis*.
Figure 5:
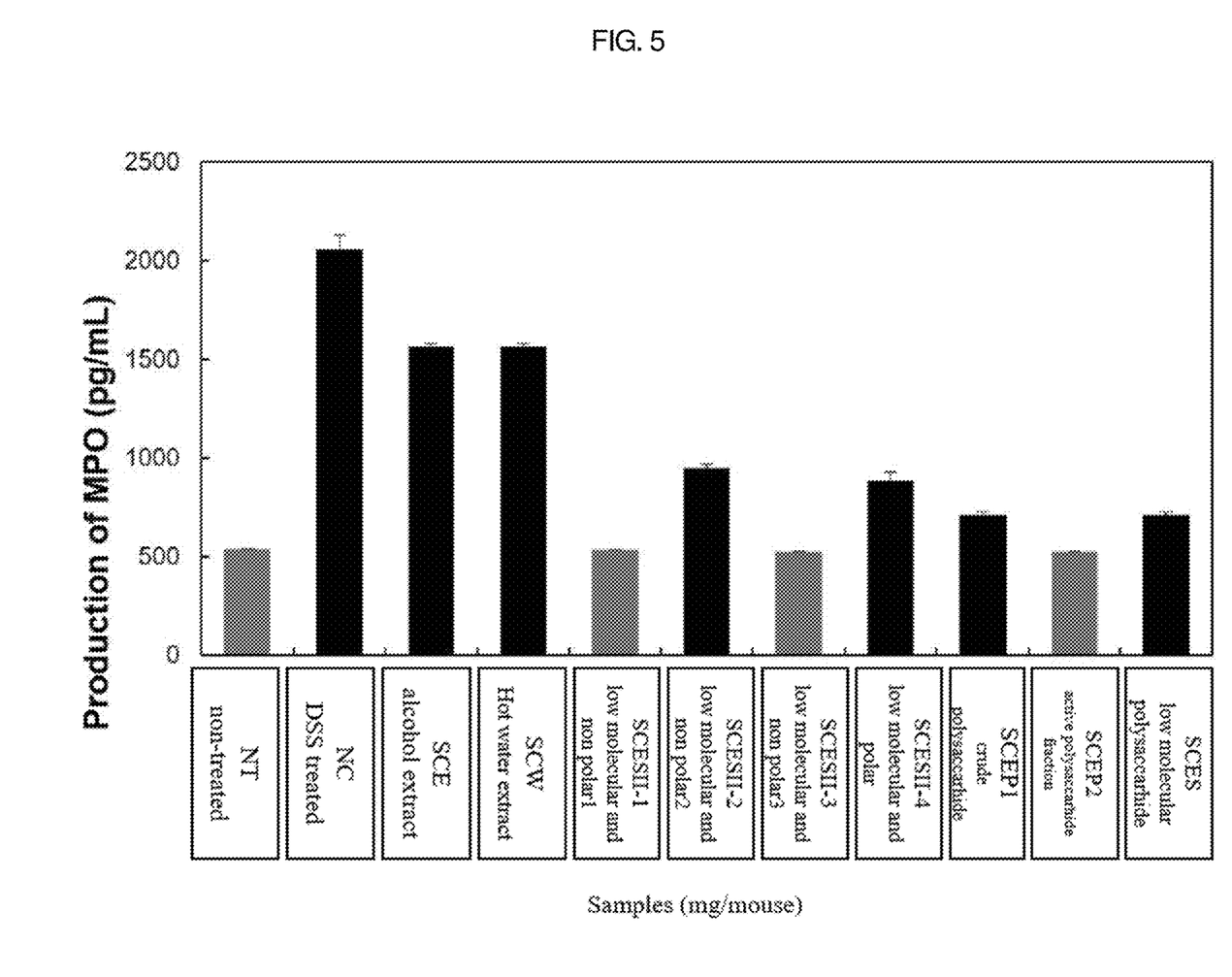
FIG. 5 is the evaluation results of MPO content in colon tissue after administration of the solvent fraction of *Saururus chinensis*.

Analysis of TNF-α and myeloperoxidase (MPO) contents was performed in colitis-induced colon tissues. The colon tissue sample was placed in a lysis buffer (Intron, Seoul, Korea) and pulverized using a homogenizer (Scilogex, Rocky hill, CT, USA). This was centrifuged at 10,000 rpm, 4° C. for 20 minutes to recover the supernatant and the TNF-α and MPO content was determined using an ELISA kit according to the manufacturer's instructions. The results are shown in FIG. 4 and FIG. 5.

As a result, in the case of the active polysaccharide fraction SCEP2 and the low molecular active fraction SCESII-1, the production of the major proinflammatory factor TNF-α was significantly reduced. In addition, in the case of inhibition of the production of MPO involved in macrophage activation, it was confirmed that polysaccharide fraction SCEP2 and low molecular active fraction SCESII-1, 3 were remarkably inhibited.

Figure 6:
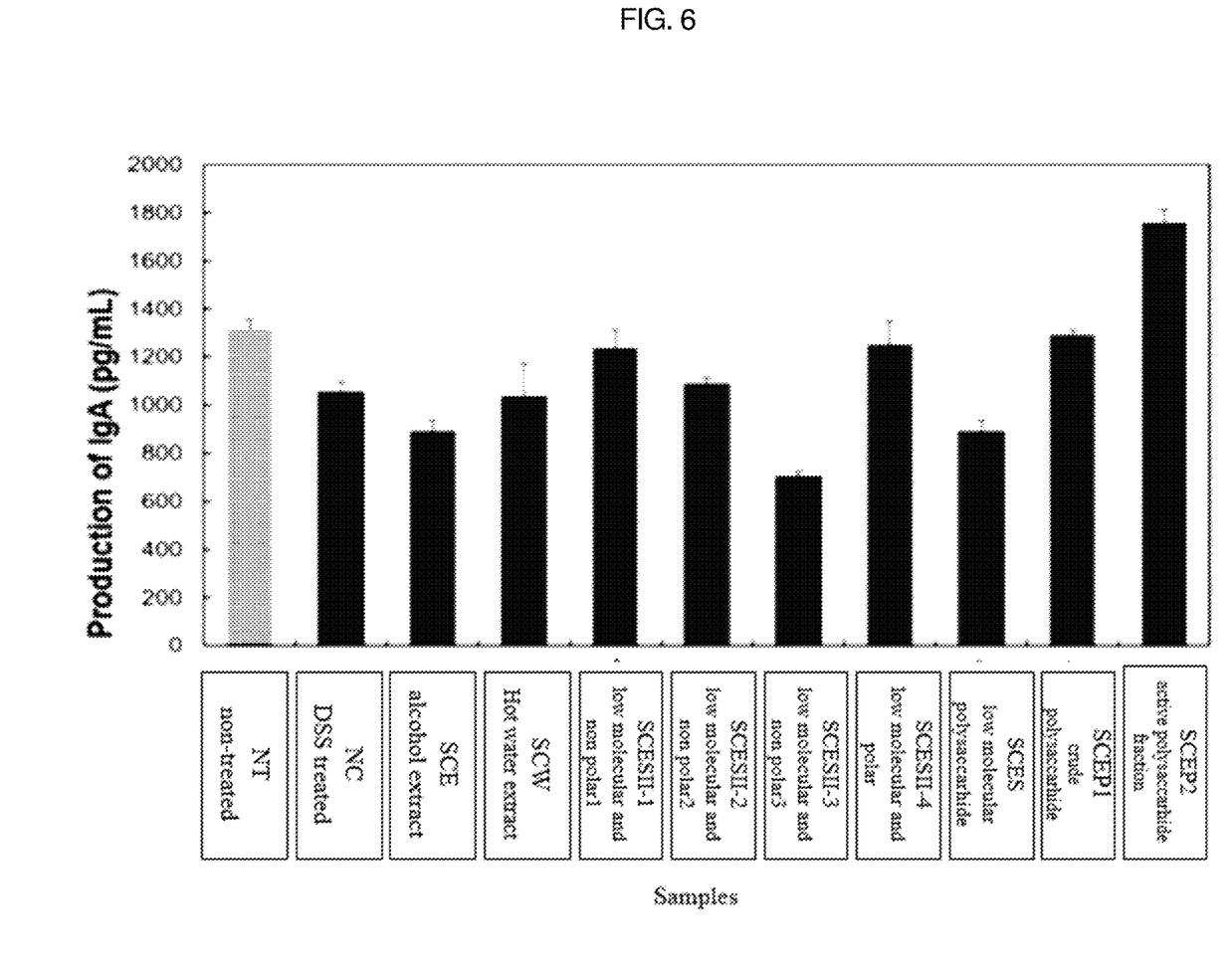
FIG. 6 is the results of evaluating the sIgA secretion ability and the related cytokine induction ability by Peyer's patches cells of the intestinal inflammation model after administration of the *Saururus chinensis* fraction.

Experimental Example 4: Evaluation of sIgA Secretion Ability and the Related Cytokine Induction Ability by Peyer's Patches Cells in Intestinal Inflammation Model 62 1-week-old C3H/HeN mice were divided into groups of 6 mice, and then, the solvent fraction of *Saururus chinensis* was orally administered a total of 10 times (once/2 days) for 20 days. Peyer's patches cells of mice were recovered and cultured in a 96-well plate for 3 days, and sIgA produced by Peyer's patches cells activated by oral administration was analyzed by ELISA. The small intestine of the mice after oral administration was removed and feces were collected, and the sIgA production ability was analyzed by ELISA. The results are shown in FIG. 6.

The evaluation results confirmed that sIgA production increased in the active polysaccharide fraction SCEP2, crude polysaccharide SCEP1, low molecular active fraction SCESII-1, and low molecular active fraction SCESII-4.

Experimental Example 5: Evaluation of SCFA-Producing Ability Induced in Feces Due to Oral Administration of the Active Solvent Fraction of *Saururus chinensis*

The cecum of the mouse after oral administration was recovered, diluted with 80% methanol to have a final concentration of 1 g/mL, filtered with a 0.45 μm syringe filter, and the ability to produce five short-chain fatty acids acids (acetic acid, propionic acid, butyric acid, valeric acid and heptanoic acid) was confirmed through gas chromatography (GC) equipped with a DBFFAP capillary column. The results are shown in Table 4 below.

It was confirmed that the active polysaccharide fraction SCEP2 and the low molecular active fraction SCESII-1 in feces increased the production of SCFA in a concentration-dependent manner. The positive control group, sulfasalazine, actually decreased the production of SCFA.

TABLE 4

| | | The production of short chain fatty acid in cecal extracts (short chain fatty acid production in cecum (μM)) | | | | | | |
|---|---|---|---|---|---|---|---|---|
| Sample | Dose (mg/mouse) | Acetic acid | Propionic acid | Butyric acid | Valeric acid | Caproic acid | Heptanoic acid | Total SCFA |
| NT | — | 10758 (64.2) | 759 (4.5) | 4200 (25.0) | 761 (4.5) | — | 290 (1.7) | 16768 (100) |
| NC | — | 5417 (63.4) | 830 (9.7) | 836 (9.8) | 774 (9.1) | 123 (1.4) | 565 (6.6) | 8545 (100) |
| PC | 2 | 3284 (56.5) | 798 (13.7) | 841 (14.5) | 513 (8.8) | — | 372 (6.4) | 5808 (100) |
| SCESII-1 | 0.5 | 4201 (60.9) | 886 (12.8) | 1207 (17.5) | 609 (8.8) | — | — | 6903 (100) |
| | 1 | 4932 (63.5) | 1001 (12.9) | 1202 (15.5) | 629 (8.1) | — | — | 7764 (100) |
| | 2 | 5130 (62.4) | 1098 (13.4) | 1379 (16.8) | 614 (7.5) | — | — | 8221 (100) |
| SCEP-2 | 0.5 | 4846 (63.2) | 797 (10.4) | 790 (10.3) | 595 (7.8) | 144 (1.9) | 500 (6.5) | 7672 (100) |
| | 1 | 5227 (64.6) | 836 (10.3) | 1419 (17.5) | 607 (7.5) | — | — | 8089 (100) |
| | 2 | 5307 (61.1) | 908 (10.4) | 1858 (21.4) | 621 (7.1) | — | — | 8689 (100) |

Experimental Example 6: Effect of the Active Ingredient Fraction of *Saururus chinensis* on Intestinal Mucus-Secreting Cells (LS 174T, a Human Intestinal Goblet Cell Line)

Figure 7:
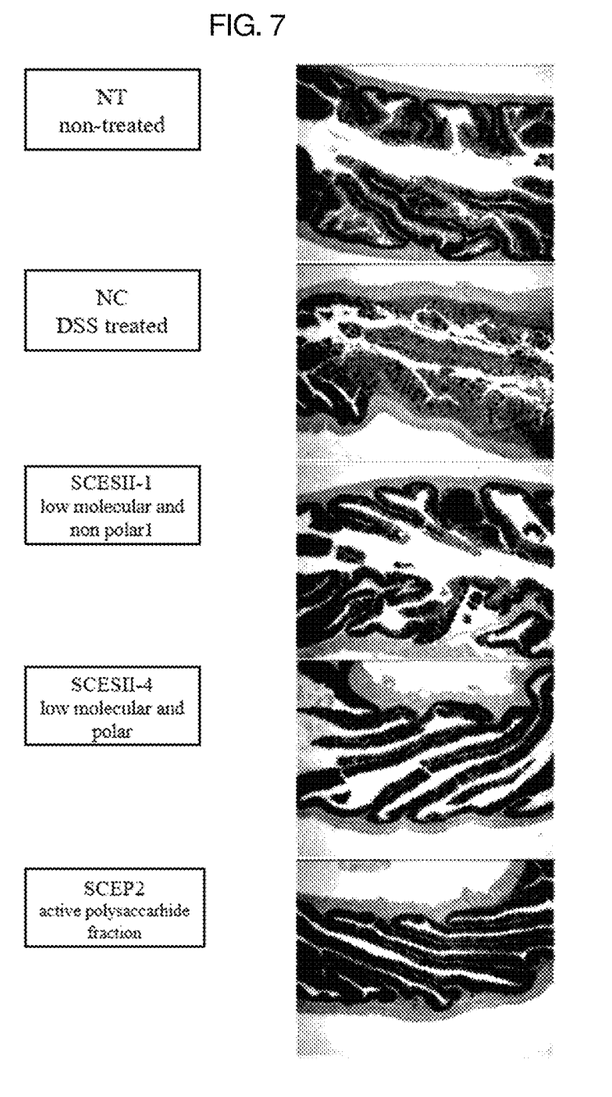
FIG. 7 is the results of evaluating the effect of the active ingredient fraction of *Saururus chinensis* on intestinal mucus-secreting cells (LS 174T, a human intestinal goblet cell line).

BALB/c mice were provided with water containing 5% DSS for 7 days, and the experimental sample was orally administered for 8 days. After sacrificing the experimental animals, tissue analysis was performed. Sections of the large intestine were fixed with 10% formalin solution, then filled with paraffin, and mounted with canada balsam. Each slide was observed using an optical microscope (40× magnification). Images were analyzed using MetaMorph software (Molecular Devices, Sunnyvale, CA, USA). The results are shown in FIG. 7.

As a result, in the case of the active polysaccharide fraction SCEP2, the low molecular active fraction SCESII-1, and the low molecular active fraction SCESII-4, the amount of Mucin (stained blue by Alcian Blue) secreted from the Goblet cells was recovered similar to that of the normal group, when compared with the normal group not treated with DSS.

INDUSTRIAL APPLICABILITY

The present disclosure relates to a composition for preventing, treating or ameliorating g inflammatory bowel disease containing a specific fraction prepared from *Saururus chinensis* as an active ingredient, and a method for preparing the same.

What is claimed is:

1. A method for preparing a solvent fraction of *Saururus chinensis* effective for inflammatory bowel disease, the method comprising the steps of:
    (S1) extracting *Saururus chinensis* with a 50-90 volume % ethanol aqueous solution,
    (S2) adding purified water to the residue remaining after the extraction, and heating to 70-100° C.,
    (S3) enzymatically treating the result of the step S2,
    (S4) removing the residue in the extract and filtering the extract,
    (S5) adding ethanol to the filtrate of the step S4 to form a precipitate, and
    (S6) obtaining the precipitate.

2. The method according to claim 1, wherein the enzyme is polygalacturonase, pectin lyase, or a mixture thereof.

3. The method according to claim 1, wherein the ethanol aqueous solution of the step S1 is a 60-80 volume % ethanol aqueous solution.

4. The method according to claim 1, wherein the step S5 is a step of concentrating the filtrate, adding more ethanol than the concentrate and stirring the mixture to form a precipitate.

5. The method according to claim 1, wherein the method further comprises a step of concentrating the precipitate after the step S6 and freeze-drying.

* * * * *